United States Patent [19]

Haradon

[11] Patent Number: 5,730,750
[45] Date of Patent: Mar. 24, 1998

[54] INTRAORAL TISSUE TRIMMING DEVICE

[76] Inventor: Geoff B. Haradon, 8782 Bellcove Cr., Colorado Springs, Colo. 80920

[21] Appl. No.: 628,912

[22] Filed: Apr. 8, 1996

[51] Int. Cl.⁶ .................................................. A61B 17/32
[52] U.S. Cl. .................................... 606/167; 433/162
[58] Field of Search ..................................... 606/167, 170, 606/174, 83, 184; 30/28; 128/750–755; 433/4, 162

[56] References Cited

U.S. PATENT DOCUMENTS

| | | |
|---|---|---|
| 617,955 | 1/1899 | Clement . |
| 865,551 | 9/1907 | Wells . |
| 973,296 | 10/1910 | Peddle . |
| 1,178,323 | 4/1916 | Knox . |
| 1,330,515 | 2/1920 | Bryant . |
| 3,997,966 | 12/1976 | Sartore . |
| 4,196,514 | 4/1980 | Merriman . |
| 4,285,344 | 8/1981 | Marshall . |
| 4,662,371 | 5/1987 | Whipple et al. ................ 606/174 |
| 4,763,669 | 8/1988 | Jaeger ............................ 606/174 |
| 5,350,391 | 9/1994 | Iacovelli ......................... 606/167 |

FOREIGN PATENT DOCUMENTS 2 600 522   12/1987   France .

*Primary Examiner*—William Lewis
*Attorney, Agent, or Firm*—Arnold, White & Durkee

[57] ABSTRACT

An instrument for trimming intraoral tissue, such as periodontal flaps, having cutting edges that are contoured to excise tissue of a predetermined shape. The instrument has first and second trimming members that may be used to stabilize the intraoral tissue prior to trimming, and may be configured at an angle for easy positioning in the mouth. The instrument may optionally include one or more finger loops and/or thumb grips.

12 Claims, 5 Drawing Sheets

INTRAORAL TISSUE TRIMMING DEVICE

BACKGROUND OF THE INVENTION

1. Field of the Invention

This invention relates generally to surgical instruments, and more specifically to dental surgery instruments for trimming intraoral tissue. In particular, this invention relates to an instrument for excising gum tissue from periodontal flaps with improved precision.

2. Description of the Related Art

Periodontal surgery often requires gum tissue to be reflected away from teeth or dental implants to gain access to roots, bone, and diseased tissues for treatment. Reflected gum tissue may be referred to as "periodontal flaps." After treatment, trimming (or recontouring) of periodontal flaps is often necessary for proper repositioning of flap tissues in the most desirable location. However, because periodontal flaps are no longer connected to teeth or dental implants, they are freestanding and difficult to stabilize for trimming with traditional instruments, such as scissors, blades and the like. Positioning of traditional instruments is often very awkward for trimming or incising periodontal flaps, especially in posterior quadrants of the mouth.

In the past, dental surgery instruments have been designed for the excision of gum and other intraoral tissue. However, none have been directed toward excision of gum tissue from periodontal flaps. In addition, most of these instruments utilize a scissor-like action, making it difficult to make precise cuts in gum or other intraoral tissue.

One known dental surgery instrument for cutting away gum tissue covering a tooth utilizes opposing dual cutting surfaces joined by two members connected together by a pivot, as in a pair of scissors. The cutting surfaces are oval shaped and are disposed at the ends of the pivoting members. These cutting surfaces are shaped to fit over a tooth (with one cutting surface on either side of the tooth) so that gum tissue that has grown over the tooth may be cut away. This type of dental instrument is not suitable for trimming or recontouring periodontal flaps, however, due to the shape of its cutting surfaces. In addition, its scissor-like action is awkward for use in the mouth, and makes precision cutting of freestanding gum tissue or other intraoral tissue difficult.

Another known dental surgery instrument designed for the excision of gum tissue also utilizes a scissor-like action. This instrument has two members connected at a pivot point with a semicircular cutting surface at the end of one member and a plate connected to the end of the other member. It is primarily designed for removing third molars and growths from the gums. The instrument is used to excise gum tissue by placing the gum tissue between the cutting surface and the plate and then drawing the members together. Its scissor-like action and enlarged cutting head make it particularly unsuitable for precision cutting of intraoral tissue, including freestanding gum tissue such as periodontal flaps.

Instruments also exist for performing other types of dental surgery, such as trimming a hard bone of the alveoli. However, these instruments also use a scissor-like action and/or have cutting surfaces of a shape unsuitable for the precise excision of freestanding gum tissue or other intraoral tissue, particularly periodontal flaps.

Existing dental surgery instruments accordingly do not provide a combination of cutting surfaces and cutting action necessary to allow freestanding gum tissue or other intraoral tissue to be excised in a precise manner. With existing dental instruments, such excisions may only be made with a degree of awkwardness and inconvenience to the surgeon.

SUMMARY OF THE INVENTION

The present invention in a broad aspect concerns a dental surgery instrument that utilizes a jaw-like trimming action together with cutting surfaces specially shaped for excision of intraoral tissue. This invention also relates to a dental surgery instrument that stabilizes freestanding intraoral tissue during excision, and that is shaped to provide easy access to all areas of the mouth.

The invention in one broad aspect comprises a manually operated, dental device which has two principal arms. One arm may be held relatively stationary in operation and is designated as a stabilizing arm. This arm has a rearward end proximal to the user and a forward or distal end for placement in the mouth. The forward or distal end terminates in a first cutting or trimming member. The distal end of the stabilizing arm may be optionally constructed to curve downward relative to the proximal end of the stabilizing arm in operation so as to fit alongside a gum line or otherwise facilitate access to intraoral tissue when positioned in the mouth. The first trimming member has a first surface or edge facing away from the user on its distal end.

A second trimming member having a second cutting surface or edge on its distal end is positioned with its cutting surface or edge opposite the cutting surface or edge of the first trimming member. The proximal end of the second trimming member may be attached to or supported from the stabilizing member to flex or otherwise move toward and away from the first trimming member. The point of such attachment or support may be at any suitable point along the stabilizing arm that enables sufficient flexure or movement of the second trimming member to effect a cutting action by the two trimming members.

The two trimming members are preferably provided with a guide member to keep them in alignment as they move relative to one another. The guide member or other separate member may serve as a linkage to keep the two trimming members linked together with a lever arm. The lever arm may be generally parallel to the stabilizing arm, but its proximal end is normally spaced from the proximal end of the stabilizing arm. The distal end of the lever arm is pivotally attached directly or indirectly to the stabilizing arm and is fulcrumed on the second trimming member such that movement of the proximal end of the lever arm toward the proximal end of the stabilizing arm causes the distal end of the lever arm to cause the distal ends of the first and second trimming members and their respective cutting surfaces or edges to be brought together to effect a cutting action.

The proximal ends of the two arms are preferably provided with means to enable a user to grip and handle the device. Thus, one or more finger holes, serrated grips or other suitable gripping means may be formed in both arms. The distal end of the second trimming member may also be provided with a viewing port and/or graduated measuring scale to enable the user to observe and measure the tissue excision process.

Embodiments of the present invention may be constructed to offer the combined advantage of providing easy access to all areas of the mouth, and stabilizing freestanding intraoral tissue while at the same time excising these tissues in a precise manner. Stabilization of freestanding intraoral tissue is provided by opposing jaw-like trimming members, which may be used to surround and support the tissue prior to trimming. According to an embodiment of the present invention, these trimming members may be attached to a stabilizing arm, which is used to position the trimming members in a mouth while remaining essentially stationary during the trimming process. Precise excision of intraoral tissue is enabled by contoured cutting edge surfaces on the trimming members, which allow excision of predetermined shapes from tissue. Precision may be further enhanced by a viewing window in the second trimming member and a graduated scale for measuring the excision process.

In another embodiment, precision and stability of excision may be further enhanced by a jaw-like trimming action provided by manipulation of a lever arm attached to the second trimming member. Unlike the scissor-like action of previous dental surgery instruments, this embodiment of the device of the present invention requires only one simple motion of a lever arm to excise the intraoral tissue.

In one preferred embodiment, the present invention also has a unique handle design contoured to allow ease of access to all areas of the mouth. In this embodiment, the stabilizing arm is curved downward to form an obtuse angle, allowing easy positioning of the device of this invention to excise intraoral tissue located on the buccal, facial, lingual or palatal areas of the mouth. In addition, the device of this embodiment may be used with equal ease to excise intraoral tissue attached to upper or lower jaws.

DETAILED DESCRIPTION OF PREFERRED EMBODIMENTS

As used herein, "intraoral tissue" includes any tissue located within a human or animal mouth. "Gum tissue" refers to any gum tissue, such as, for example, periodontal flaps. "Biopsy tissue" includes gum, mucousal, tongue or any other intraoral tissue that may be subject to excision for biopsy. The term "mouth" may be used interchangeably with the term "oral cavity." The "rearward" or "proximal" end of an embodiment of the device of the present invention is that end of the device which is designed to be manipulated by a user's hand or hands to achieve a trimming action. The "forward" or "distal" end of an embodiment of the device of the present invention is that end of the device designed to be inserted into a mouth for trimming or gum tissue or other intraoral tissue. When used to describe an element of an embodiment of the present invention, the term "rearward" or "proximal" refers to an end of the element that is disposed toward, or nearer to, a user when the device is in service. The term "forward" or "distal" refers to the opposite end of the element that is disposed toward a mouth when the device is in service.

Apparatus

Figure 1:
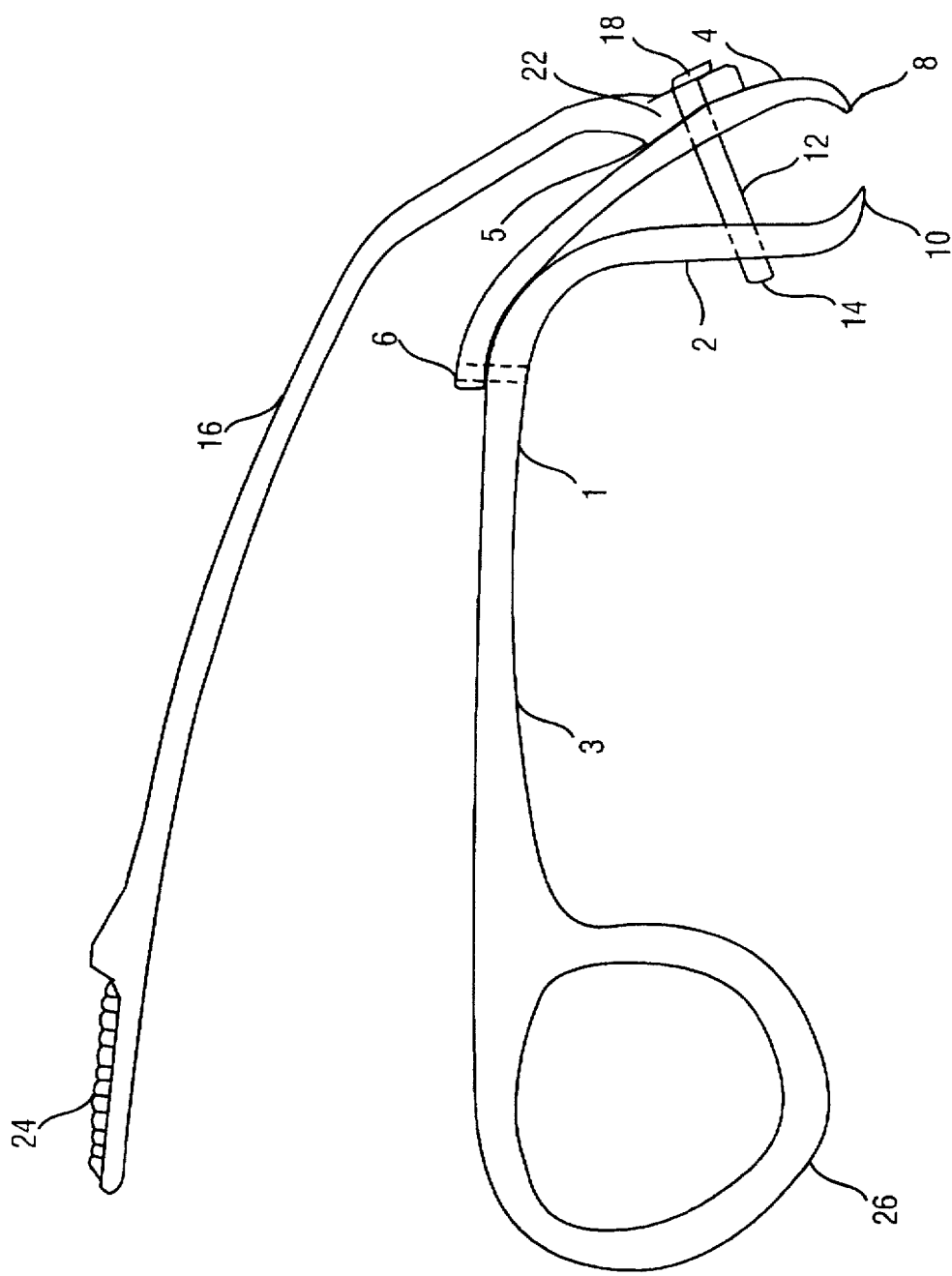
FIG. 1 is a cross-sectional view of one embodiment of an intraoral tissue trimmer according to the present invention.

FIG. 1 is a cross-sectional view of a preferred embodiment of an intraoral tissue trimming device according to the present invention that is designed to excise gum tissue from periodontal flaps. In FIG. 1, stabilizing arm 1 forms the base of the intraoral tissue trimming device. The stabilizing arm 1 includes three basic elements: first trimming member 2, stabilizing member 3, and finger loop 26. Second trimming member 4 is connected or attached at the proximal end to stabilizing arm 1 by rivet 6, welded joint, or other suitable means known to the art. The point of such attachment or support may be at any suitable point along the stabilizing arm that enables sufficient flexure or movement to effect a cutting action by the two trimming members. Second cutting edge 8 and first cutting edge 10 are provided at the distal ends of second trimming member 4 and first trimming member 2, respectively. Second trimming member 4 and first trimming member 2 are disposed opposite each other in trimming relation.

Figure 2:
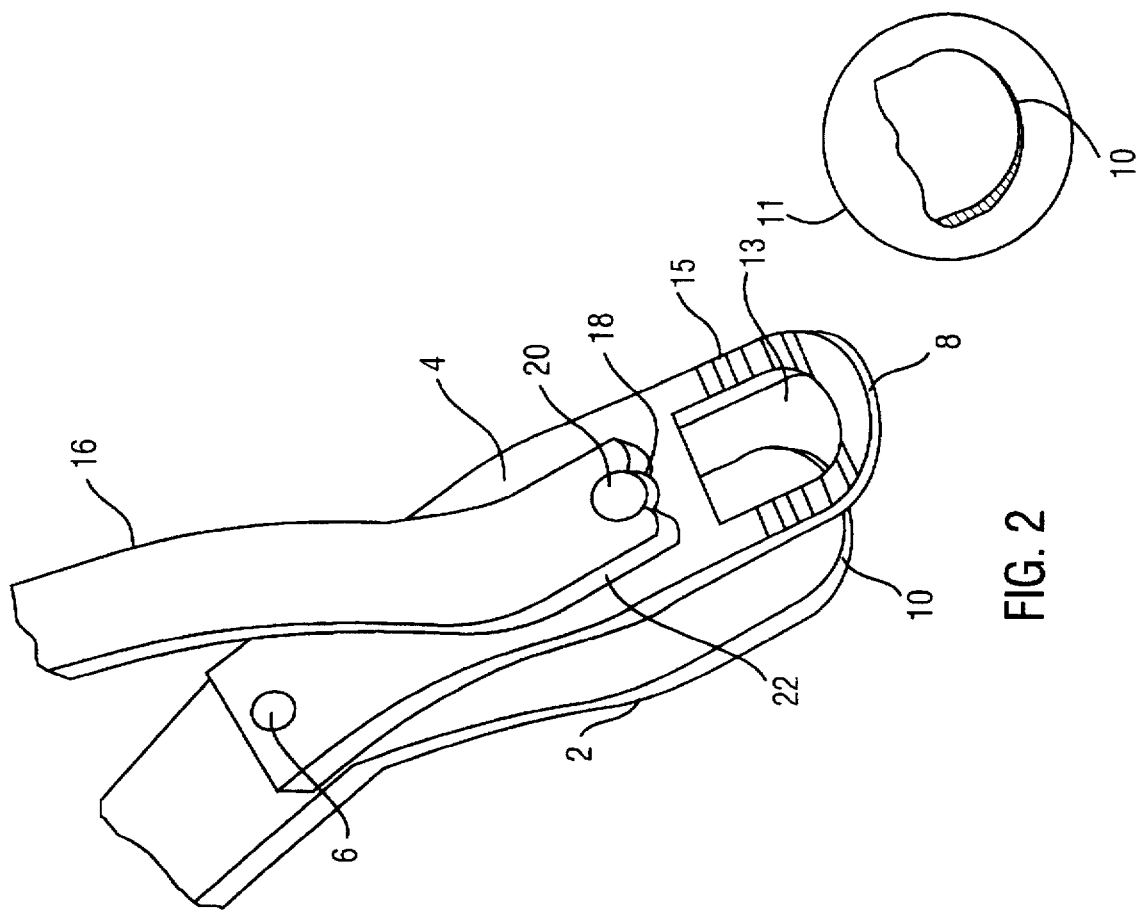
FIG. 2 is a partial frontal perspective view of the intraoral tissue trimmer of FIG. 1, showing trimming members and lever arm.

As shown in FIG. 2, a convex-shaped exterior cutting edge 8 may be formed on the distal end of second trimming member 4, and a corresponding convex-shaped cutting edge 10 may be formed on the distal end of first trimming member 2 (as fully shown in section 11 of FIG. 2). Thus formed, cutting edges 8 and 10 are designed to fit together in cutting relation to excise a desired area of gum tissue when the surface of first cutting edge 10 contacts the surface of second cutting edge 8. In addition to convex-shaped cutting edges, one skilled in the art will recognize that cutting edges 8 and 10 may also be of any shape appropriate for excision of intraoral tissue, including excision of tissue from maxillary and mandibular incisors, canine, premolar and molar teeth, and dental implants. Cutting edges 8 and 10 may also be of any shape appropriate for excision of biopsy tissue. Those skilled in the art will also recognize that cutting edge shapes may be of varying sizes as needed for specific applications.

As shown in FIG. 2, viewing window 13 may be formed within the distal end of second trimming member 4 to allow tissue to be viewed during an excision process, thereby allowing increased precision. In addition, precision may be further increased by providing a graduated scale 15 and/or other measuring means on at least one edge of window 13, so that an amount of tissue excised may be measured during an excision process. While one embodiment of a viewing window with graduated scale is shown in FIG. 2, it will be understood by those skilled in the art that the present invention may be practiced with viewing windows of varying sizes and shapes including, but not limited to, circular, semicircular, rectangular, oval or irregular in shape. Those skilled in the art will also recognize that benefits of this invention may be obtained with any suitable type of graduated scale known to the art, including scales based on differing systems of measurement (such as english or metric) or having arbitrary spacing, scales having even or uneven spacing, and/or scales which are positioned around the entire perimeter of a viewing window, or any portion or edge thereof. In one embodiment, the graduated scale may be marked off in millimeters. In addition, a graduated scale may be formed and positioned on any surface of a second trimming member, or alternatively on a first trimming member, that is in a location suitable for providing guidance during an excision process. Finally, those skilled in the art will understand that the present invention may also be practiced successfully in the absence of a viewing window and/or graduated scale.

As shown in FIG. 1, both second trimming member 4 and first trimming member 2 may be provided with aligned openings through which fulcrum pin 12 or other suitable linkage and/or guide member known to the art extends. One end of fulcrum pin 12 is secured to first trimming member 2 by means of rivet head 14 or other suitable restraining means known to those skilled in the art. The other end of fulcrum pin 12 extends through notch 20 (FIG. 2) in one end of lever arm 16. Fulcrum pin 12 is secured to lever arm 16 by means of a rivet head 18 that is larger than notch 20, or by other suitable means known to those skilled in the art.

The distal end of lever arm 16 is provided with fulcrum head 22, which contacts second trimming member 4 at fulcrum point 5, located at point generally intermediate between the proximal and distal ends of the exterior surface of second trimming member 4. By "exterior surface" it is meant the surface of second trimming member 4 disposed toward the lever arm. Although one embodiment of a fulcrum head is shown in FIG. 1, a fulcrum head may be of any shape or design known to the art that is suitable for transferring leverage from a lever arm to trimming members, including those designs that may be integral to a lever arm, trimming member, and/or fulcrum pin. In addition to being located on the exterior surface at a point generally intermediate between proximal and distal ends of the second trimming member, a fulcrum point may be located on any surface and at any suitable point along a trimming member which enables sufficient leverage to be transmitted from a lever arm to effect a cutting action by the trimming members.

The proximal end of lever arm 16 has thumb grip 24, which is preferably contoured to fit a thumb in a comfortable manner and which is preferably serrated to prevent slippage. So oriented, when lever arm 16 is depressed downward in relation to the stabilizing arm 1, fulcrum head 22 simultaneously depresses second trimming member 4, thereby causing second trimming member 4 to be deflected downward toward first trimming member 2, bringing cutting edges 8 and 10 together so that a cutting action is achieved. In a preferred embodiment, substantially all movement of lever arm 16 is transferred to second trimming member 4, with first trimming member 2 remaining substantially static. However, those skilled in the art will recognize that benefits of the present invention may also be obtained with a first trimming member that is deflected, either alone or in concert with a second trimming member.

To hold first trimming member 2 in place during the trimming operation, finger loop 26 is provided on proximal end of stabilizing arm 1 so that the intraoral tissue trimming device may be held in place by an index or other finger inserted into finger loop 26, while cutting action is provided by a thumb depressed against thumb grip 24. Although one embodiment of the present invention having a thumb grip and finger loop is illustrated in FIG. 1, those skilled in the art will appreciate that the benefit of the present invention may be achieved with the use of finger loops and thumb grips of different design, or in the absence of any loops or grips at all. When present, the thumb grip and finger loop may have any suitable configuration known to those skilled in the art, including those having multiple finger loops and nonserrated edges.

Figure 4:
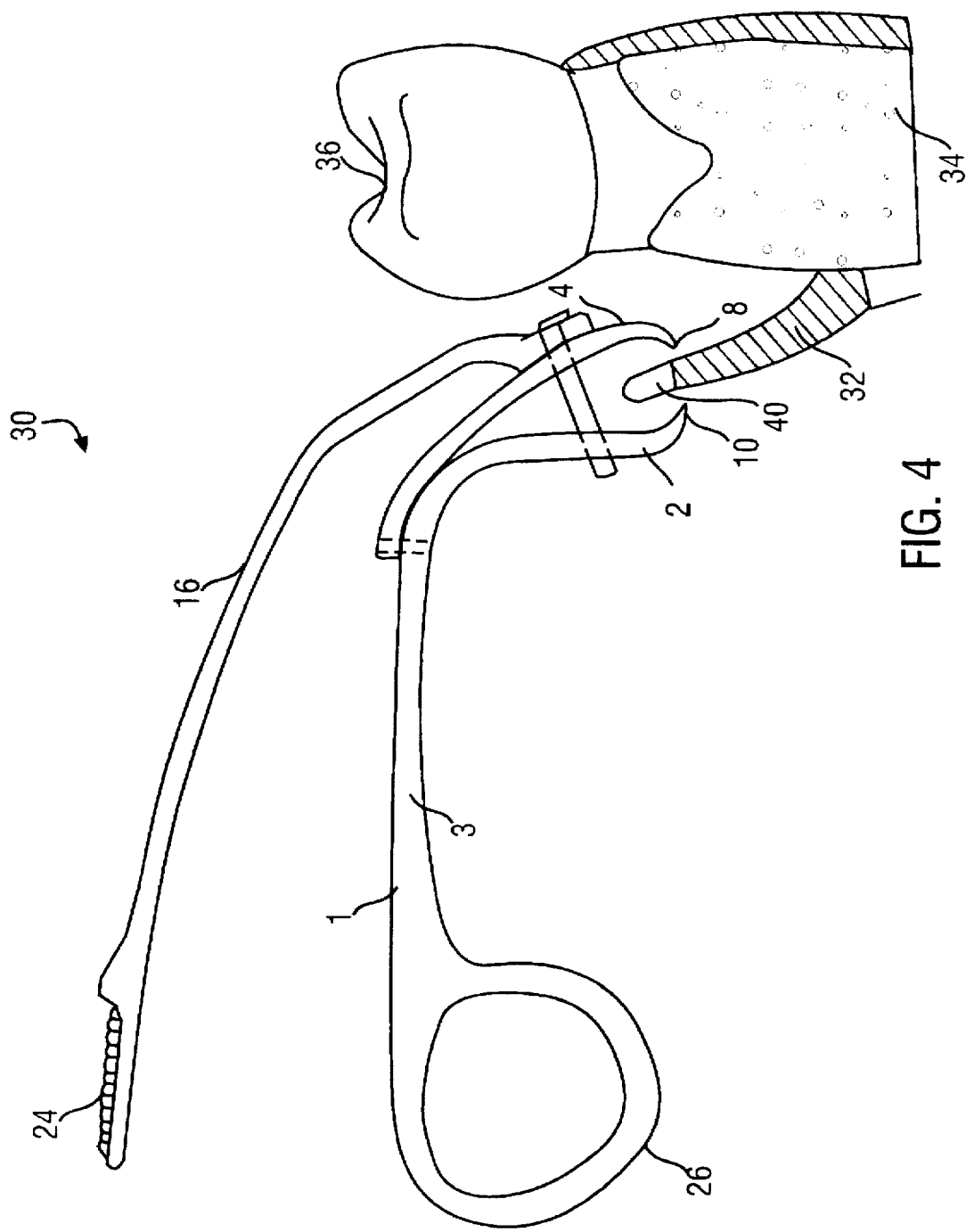
FIG. 4 is a side cross-sectional view of one embodiment of an intraoral tissue trimming device according to the present invention shown with trimming members in open position just prior to excision of buccal flap tissue
Figure 5:
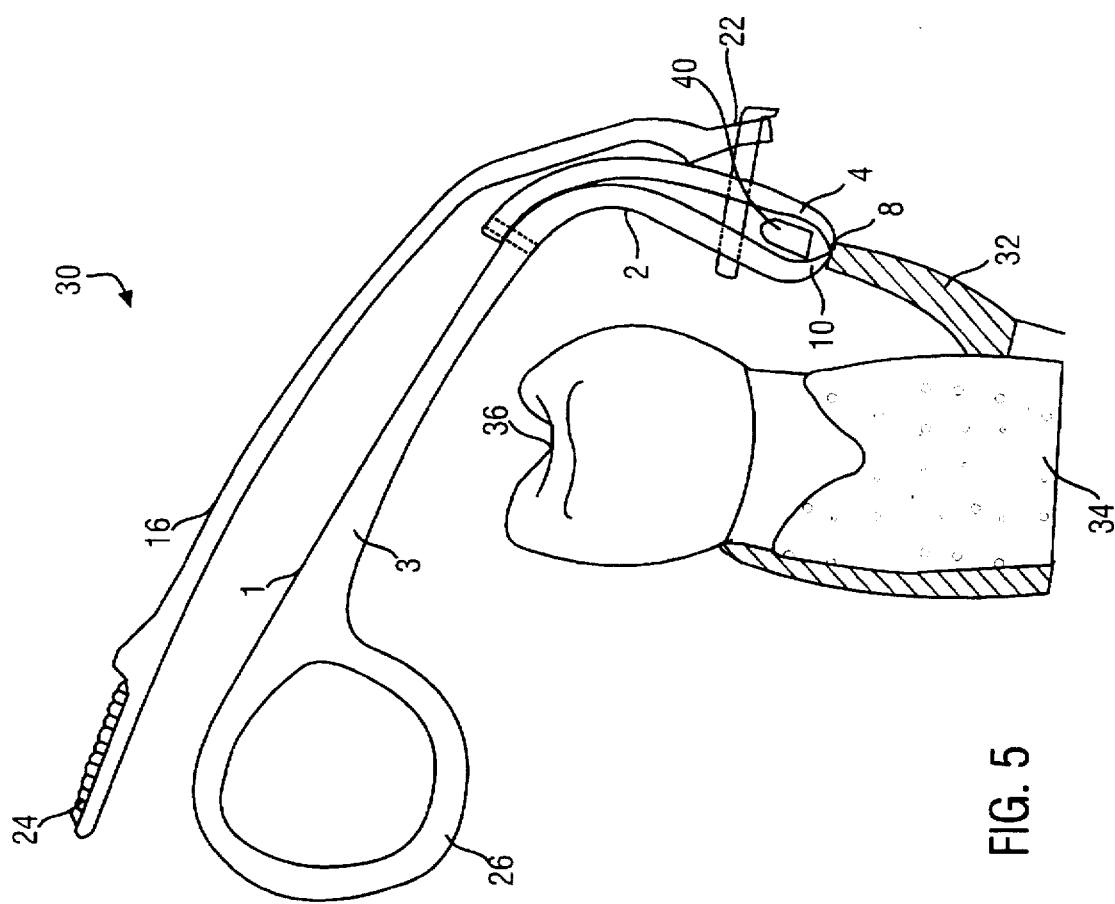
FIG. 5 is a side cross-sectional view of one embodiment of an intraoral tissue trimming device according to the present invention shown with trimming members in closed position following excision of lingual flap tissue.

In one embodiment of the present invention illustrated in FIG. 1, stabilizing arm 1 is curved downward so that that first trimming member 2 forms an obtuse angle with stabilizing member 3. Lever arm 16 is curved in a manner complementary to the angle of stabilizing arm 1. The angled shape of stabilizing arm 1 and lever arm 16 allow an intraoral tissue trimming device according to the present invention to be used to trim gum tissue located essentially anywhere in the mouth. As shown in FIGS. 4 and 5, the device may be positioned using stabilizing arm 1 to allow easy access to gum tissue positioned on facial, buccal, lingual, or palatal sides of all maxillary and mandibular teeth or dental implants.

In the practice of this invention, first trimming member 2 is preferably positioned at an angle of greater than about 90 degrees and less than about 180 degrees relative to the stabilizing member 3. However, it will be recognized by those skilled in the art that the benefits of this invention may also be realized with a first trimming member positioned at an angle of less than about 90 degrees or greater than about 180 degrees to a stabilizing arm. Those skilled in the art will also appreciate that the benefits of this invention may be realized with instruments having members constructed of varying relative dimensions, or in the absence of one or more of the members illustrated in FIG. 1.

In the practice of this invention, an intraoral tissue trimming device may be constructed in any size necessary to fit a particular application. For example, relatively small sized instruments may be constructed for trimming intraoral tissue in infants, persons with small mouths, or small animals. Relatively large instruments may be constructed for trimming intraoral tissue in larger human mouths and the mouths of large animals.

The intraoral tissue trimming device of this invention may be constructed of any suitable material known to those skilled in the art including, but not limited to, plastics, ceramics, steel, aluminum, other metals or combinations thereof.

In addition, it will also be understood that the intraoral tissue trimming device of the present invention may be constructed in a variety of shapes to fit particular applications. For example, the contour of stabilizing and lever arms and the shape of cutting edge surfaces may be tailored for removal of certain or specific intraoral growth including, but not limited to, biopsy tissue and gum tissue located in essentially any area of a mouth, including facial, buccal, lingual, or palatal areas and/or on all maxillary and mandibular teeth or dental implants.

Use of Apparatus

Figure 3:
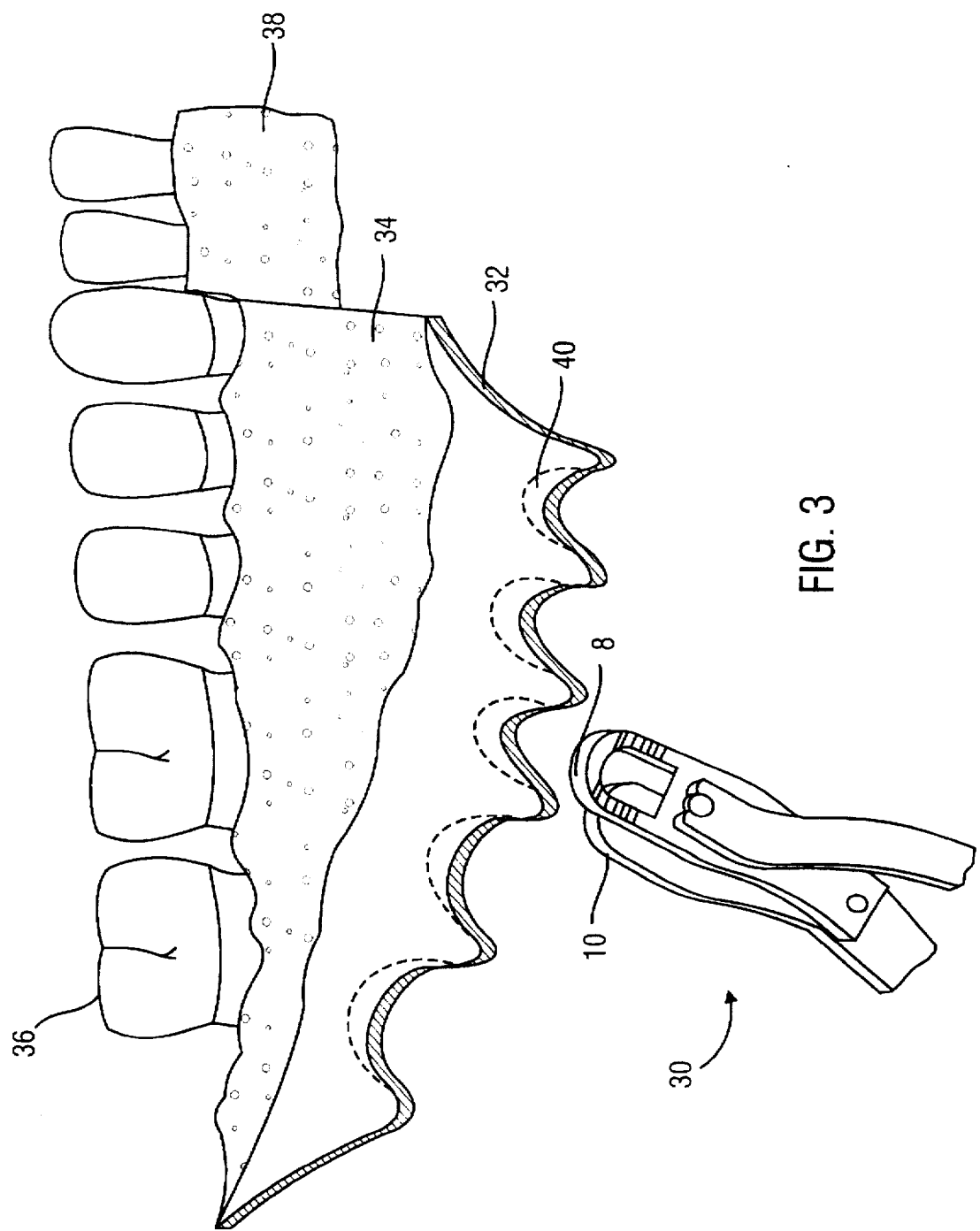
FIG. 3 illustrates the front part of an intraoral tissue trimming device according to the present invention in close proximity to periodontal flaps that are ready for trimming.

FIG. 3 illustrates the distal end of one embodiment 30 of an intraoral tissue trimming device according to the present invention in close proximity to gum tissue that is ready to be excised. In this illustration, gum tissue consists of periodontal flaps 32 cut from other gum tissue 38, and reflected away from bone 34 and teeth 36. As illustrated in FIG. 3, this embodiment of the intraoral tissue trimmer has convex cutting edges 8 and 10 contoured to trim and excise predetermined shapes of gum tissue 40 from periodontal flaps 32.

In FIG. 4, the same embodiment 30 of an intraoral tissue trimming device is shown in position ready to excise gum tissue from freestanding, periodontal flaps 32 located on the buccal surface of a mandibular posterior tooth 36. In preparation for excising the gum tissue 40 from periodontal flaps 32, trimming members 2 and 4 of the intraoral tissue trimming device may be described as being "open" so that they may be placed in a position to straddle periodontal flaps 32. Trimming members 2 and 4 are placed in this position by manipulating stabilizing arm 1 with a finger placed through finger loop 26, and with a thumb on thumb grip 24. In this position, freestanding periodontal flaps 32 may be stabilized for trimming by contact with the trimming members prior to the trimming operation. At this point in the gum trimming process, the intraoral trimming device may be held substantially stationary in position by a finger inserted in finger loop 26, such that trimming members 2 and 4 are held in place around the periodontal flaps 32 in a stabilizing manner.

Further stabilization may be provided by a thumb placed on the thumb grip 24.

In FIG. 5, excision of gum tissue 40 from periodontal flaps 32 using the same embodiment 30 of an intraoral tissue trimming device according to the present invention is illustrated. In this case, the periodontal flaps are located on the lingual surface of a mandibular posterior tooth 36. As shown in FIG. 5, trimming members 2 and 4 have been positioned around periodontal flaps 32 so that gum tissue 40 may be excised. During the cutting operation, stabilizing arm 1 may be held substantially stationary in place by a finger inserted in finger loop 26, while lever arm 16 may be depressed by a thumb placed on thumb grip 24 such that fulcrum head 22 causes trimming members 2 and 4 to be compressed and cutting edges 8 and 10 to be brought together around periodontal flaps 32. When depressed far enough, lever arm 16 causes cutting edges 8 and 10 to contact each other, thus excising gum tissue 40 in such a way that a precise incision may be made into the periodontal flaps 32 that is of the shape of the contoured cutting edges 8 and 10. When cutting edges 8 and 10 are brought together in this way, trimming members 2 and 4 may be described as being in "closed" position.

Although FIGS. 3–5 illustrate one embodiment of an intraoral trimming device according to the present invention, it should be understood that the present invention may be used to trim other types of intraoral tissue that may be present in a mouth, including biopsy tissue and gum tissue on or around dental implants. In addition, intraoral tissue may be trimmed in essentially any location in the mouth using embodiments of a device according to the present invention having differing configurations and by using any suitable technique known to those skilled in the art to manipulate first and second trimming members. Finally, it should be understood that the present invention may be used to trim or excise intraoral tissue from animals as well as humans.

Although the invention has been described by reference to preferred embodiments, it is not intended that the novel methods and apparatus be limited thereby, but various modifications are intended to be included as following within the spirit and broad scope of the foregoing disclosure and the following claims.

What is claimed is:

1. A method for trimming intraoral tissue, comprising the steps of:
   providing a stabilizing arm having distal and proximal ends;
   providing first and second trimming members having distal and proximal ends, wherein said first and second trimming members have first and second cutting edges, respectively, said cutting edges being formed on the distal ends of said trimming members, and wherein the distal end of the second trimming member is fastened to the stabilizing arm;
   positioning the first and second cutting edges on opposing sides of intraoral tissue; and
   trimming the intraoral tissue by causing the first and second trimming members to be brought together so that the first and second cutting edges contact each other.

2. The method of claim 1, further comprising the step of stabilizing the intraoral tissue between the first and second trimming members prior to trimming the intraoral tissue.

3. The method of claim 2, wherein the first and second cutting edges are shaped to make incisions of predetermined shape in the intraoral tissue.

4. The method of claim 3, wherein the first cutting edge has a convex shape, and wherein the second cutting edge has a convex shape corresponding to the convex shape of the first cutting edge.

5. The method of claim 2, wherein the distal end of the second trimming member has a viewing window formed therein, and further comprising the step of observing the intraoral tissue through the viewing window.

6. The method of claim 2, wherein a graduated scale is formed on the distal end of at least one of the first or second trimming members, and further comprising the step of measuring the intraoral tissue to be trimmed.

7. The method of claim 4, wherein the first trimming member is part of a stabilizing arm, wherein the second trimming member is connected to a lever arm, and further comprising the steps of:
   positioning the first and second trimming members by manipulating the stabilizing arm and the lever arm;
   holding the first trimming member in a substantially static position using the stabilizing arm; and
   depressing the lever arm to bring the second trimming member into contact with the first trimming member.

8. The method of claim 7, further comprising trimming the gum tissue from periodontal flaps.

9. A device for excising gum tissue from periodontal flaps, comprising:
   a stabilizing arm comprising a first trimming member and a stabilizing member, wherein said first trimming member is disposed at a distal end of the stabilizing arm and said stabilizing member is disposed at a proximal end of the stabilizing arm, and wherein said first trimming member has distal and proximal ends and is configured substantially at an obtuse angle to the stabilizing member;
   a second trimming member having distal and proximal ends, wherein the proximal end of said second trimming member is fastened to the stabilizing arm so that the distal end of the second trimming member is juxtaposed in an opposing relationship from the distal end of the first trimming member;
   a first cutting edge formed on the distal end of the first trimming member, wherein said first cutting edge has a convex shape;
   a second cutting edge formed on the distal end of the second trimming member, wherein said second cutting edge has a convex shape corresponding to the convex shape of the first cutting edge, and wherein the second cutting edge is juxtaposed in an opposing cutting relationship from the first cutting edge;
   a viewing window formed in the distal end of the second trimming member;
   a graduated measuring scale formed on the distal end of the second trimming member, said graduated scale positioned adjacent to at least a portion of the perimeter of the viewing window;
   a curved lever arm for selectively positioning the first and second cutting edges relative to each other and having distal and proximal ends, wherein the distal end of the lever arm is configured to have a fulcrum head with a retaining slot disposed therein, and wherein said fulcrum head is fastened to the first and second trimming members by means of a fulcrum pin anchored in said retaining slot and extending through an opening formed in the second trimming member adjacent to its distal end to a point where said fulcrum pin is anchored to the first trimming member adjacent to its distal end in such a way that the proximal end of the lever arm is disposed adjacent to the proximal end of the stabilizing arm;

a finger loop formed on the proximal end of the stabilizing arm, wherein said finger loop is adapted for the insertion of a finger; and a serrated thumb grip formed on the proximal end of the lever arm, wherein said thumb grip is adapted to receive a thumb for depressing the lever arm.

10. A device for trimming intraoral tissue, comprising:

a stabilizing arm comprising a first trimming member and a stabilizing member, and having distal and proximal ends, wherein said first trimming member has distal and proximal ends, and wherein said first trimming member is disposed at the distal end of the stabilizing arm and said stabilizing member is disposed at the proximal end of the stabilizing arm;

a second trimming member having distal and proximal ends, wherein the proximal end of said second trimming member is fastened to the stabilizing arm;

a first cutting edge formed on the distal end of the first trimming member;

a second cutting edge formed on the distal end of the second trimming member;

a lever arm having distal and proximal ends, wherein the distal end of the lever arm is configured to have a fulcrum head, and wherein said fulcrum head is fastened to the first and second trimming members between the proximal and distal ends of the trimming members; and a graduated scale formed on the distal end of at least one of the first or second trimming members;

wherein the second cutting edge is juxtaposed in an opposing cutting relationship with the first cutting edge, and wherein the first and second cutting edges are shaped to make incisions of predetermined shape into the intraoral tissue.

11. A device for trimming intraoral tissue, comprising:

a stabilizing arm comprising a first trimming member and a stabilizing member, and having distal and proximal ends, wherein said first trimming member has distal and proximal ends, wherein said first trimming member is disposed at the distal end of the stabilizing arm and said stabilizing member is disposed at the proximal end of the stabilizing arm, and wherein the first trimming member is configured at an obtuse angle to the stabilizing member;

a second trimming member having distal and proximal ends, wherein the proximal end of said second trimming member is fastened to the stabilizing arm;

a first cutting edge formed on the distal end of the first trimming member;

a second cutting edge formed on the distal end of the second trimming member; and a lever arm having distal and proximal ends, wherein the distal end of the lever arm is configured to have a fulcrum head, wherein said fulcrum head is fastened to the first and second trimming members between the proximal and distal ends of the trimming members, wherein the lever arm is curved so that the proximal end of the lever arm is disposed adjacent to the proximal end of the stabilizing arm, wherein the fulcrum head has a retaining slot disposed therein, and wherein the fulcrum head is fastened to the first and second trimming members by means of a fulcrum pin anchored in said retaining slot;

wherein the second cutting edge is juxtaposed in an opposing cutting relationship with the first cutting edge, and wherein the first and second cutting edges are shaped to make incisions of predetermined shape into the intraoral tissue, said first cutting edge having a convex shape, and said second cutting edge having a convex shape corresponding to the convex shape of the first cutting edge.

12. The device of claim 11, further comprising a finger loop formed on the proximal end of the stabilizing arm and a serrated thumb grip formed on the proximal end of the lever arm.

* * * * *